United States Patent [19]
Sakurai et al.

[11] Patent Number: 5,716,626
[45] Date of Patent: Feb. 10, 1998

[54] SKIN CLEANSER

[75] Inventors: Naoe Sakurai; Hikaru Sumida; Takashi Komori, all of Tokyo, Japan

[73] Assignee: Kao Corporation, Tokyo, Japan

[21] Appl. No.: 568,977

[22] Filed: Dec. 7, 1995

[30] Foreign Application Priority Data

Feb. 21, 1995 [JP] Japan ................... 7-058065
Jul. 7, 1995 [JP] Japan ................... 7-196165

[51] Int. Cl.⁶ ................... A61K 7/48; A61K 9/10
[52] U.S. Cl. ................... 424/401; 424/78.03; 514/938; 514/944; 514/945
[58] Field of Search ................... 424/401, 78.03; 514/938, 944, 945; 252/DIG. 5

[56] References Cited

U.S. PATENT DOCUMENTS 3,261,753   7/1966   Gotte et al.

FOREIGN PATENT DOCUMENTS

| | | |
|---|---|---|
| 0 037 161 | 10/1981 | European Pat. Off. |
| 0 051 232 | 5/1982 | European Pat. Off. |
| 0 070 074 | 1/1983 | European Pat. Off. |
| 0 150 949 | 8/1985 | European Pat. Off. |
| 0 207 642 | 1/1987 | European Pat. Off. |
| 0 358 216 | 3/1990 | European Pat. Off. |
| 0 490 041 | 6/1992 | European Pat. Off. |
| 0 586 234 | 3/1994 | European Pat. Off. |
| 2 324 288 | 4/1977 | France. |
| 2 370 090 | 6/1978 | France. |
| 1 807 338 | 8/1969 | Germany. |
| 2 008 777 | 11/1970 | Germany. |
| 43 15 396 | 11/1994 | Germany. |
| 5-132700 | 5/1993 | Japan. |
| 5-506259 | 9/1993 | Japan. |
| 95/30737 | 11/1995 | WIPO. |

OTHER PUBLICATIONS

Chemical Abstracts, vol. 96, No. 2, Jan. 11, 1982, AN-11503z, JP-A 08 182 897, Jul. 6, 1981.

*Primary Examiner*—Raj Bawa
*Attorney, Agent, or Firm*—Oblon, Spivak, McClelland, Maier & Neustadt, P.C.

[57] ABSTRACT

The skin cleanser of the present invention makes it possible to thoroughly wash off oily stains such as makeup articles (lipstick, eye-make, waterproof foundation, etc.) while giving a good feel in use.

A detergent composition containing the following components (A) and (B) is packed in a foamer container 10 provided with a porous membrane:

(A) at least one anionic surfactant having a branched hydrocarbon group selected from phosphate surfactants, sulfate surfactants and sulfonate surfactants; and (B) at least one nonionic surfactant.

14 Claims, 1 Drawing Sheet

Fig. 1

SKIN CLEANSER

FIELD OF THE INVENTION

This invention relates to a skin cleanser wherein a detergent composition is packed in a roamer container. More particularly, it relates to a skin cleanser which imparts a good feel in use, has a high detergency and gives creamy foam with good shape retention.

BACKGROUND OF THE INVENTION

There have been developed foamable detergent compositions, which are to be discharged from a foamer container in the state of foam prior to use, for various purposes including bathing preparations, face cleansers and hair shampoos. Also, various attempts have been made to develop a foamer container from which a detergent composition can be discharged in the state of stable foam. For example, JP-B-52-16567 proposes a container in which a detergent composition is mixed with air and then passed through a foaming means (a porous material, etc.) resulting in discharge of foam (the term "JP-B" as used herein means an "examined Japanese patent publication").

As a foamable detergent composition to be discharged from such a foamer container in the state of foam with fine texture, JP-A-5-132700 proposes those containing surfactants, monohydric alcohols and polyhydric alcohols (the term "JP-A" as used herein means an "unexamined published Japanese patent application"). Also, WO91/14759 corresponding to JP-W-5-506259 proposes to pack a detergent composition, which contains a less irritative surfactant at a relatively low concentration and a water-soluble polymer, in a squeeze-type foamer container in order to sustain the concentration of the surfactant on the skin to a definite level for a prolonged period of time to thereby cleanse the skin at a high reproducibility while suppressing skin irritation (the term "JP-W" as used herein means a "PCT application published in Japan").

However, a detergent composition packed in a conventional foamer container has a problem that it has a high foam density and poor shape retention. Therefore, the foam discharged from the foamer container would disappear during skin massage therewith, thus failing to give any satisfactory massage. There arises another problem that stains, which can be hardly washed away, cannot fully eliminated with the foam. This has been a serious problem particularly in the cases of washing off makeup articles which are highly resistant against sweat, etc. and hair care products which contain polymers with a relatively low solubility in water and thus have good hair setting performance.

An object of the present invention is to solve these problems encountering in the prior arts by providing a skin cleanser which imparts a good feel in use, has a high detergency and gives creamy foam with good shape retention.

SUMMARY OF THE INVENTION

The present inventors have found out that stains, which have been regarded as being hardly eliminated, can be fully washed off while achieving a good feel in use by packing a detergent composition, which comprises a nonionic surfactant and an anionic surfactant, in a foamer container provided with a porous membrane and discharging the detergent composition in the state of foam via the porous membrane. The present invention has been completed based on this finding.

Accordingly, the present invention provides a skin cleanser comprising a detergent composition containing the following components (A) and (B) is packed in a foamer container provided with a porous membrane:

(A) at least one anionic surfactant having a branched hydrocarbon group selected from phosphate surfactants represented by the formula (1), sulfate surfactants represented by the formula (2) and sulfonate surfactants represented by the formula (3):

(1)

(2)

(3)

wherein, in the formula (1), $R^1$ represents a hydrocarbon group having 5 to 13 carbon atoms and $R^2$ represents a hydrocarbon group having 5 to 11 carbon atoms, provided that the sum of the carbon atoms in $R^1$ and $R^2$ is from 12 to 22, and $X^1$ and $X^2$ independently represent a hydrogen atom, an alkali metal, ammonium, a basic amino acid residue or an alkanolamine residue carrying a hydroxyalkyl group having 2 to 3 carbon atoms; and in the formulae (2) and (3), $R^3$ represents a branched hydrocarbon group having 6 to 24 carbon atoms, Y represents an oxyethylene group, a is a number of from 0 to 10, $R^4$ represents a branched or a linear hydrocarbon group having 6 to 24 carbon atoms, Z is a group represented by any of the following formulae (4) to (9):

(4)

(5)

(6)

(7)

(8)

(9)

wherein, in the formulae (4) to (9), $R^5$ represents a hydrogen atom or a hydrocarbon group having 10 to 14 carbon atoms and b is a number of 0 to 10; M represents a hydrogen atom, an alkali metal, ammonium, a basic amino acid residue, an alkanolamine residue carrying a hydroxyalkyl group having 2 to 3 carbon atoms or an aliphatic alkanolammonium and n is the valence of M;

(B) at least one nonionic surfactant.

BRIEF DESCRIPTION OF THE DRAWING

10: foamer container,
11: body of container,
13: gas/liquid mixing unit,
13b: porous membrane,
15: nozzle,
18: discharge port,
18a: porous membrane-fixing member,
18b: porous membrane,
X: foam-discharge channel, and
Y: air-return channel.

Next, the present invention will be described in greater detail.

DETAILED DESCRIPTION OF THE INVENTION

In the present invention, at least one anionic surfactant is used as the component (A). Preferably those anionic surfactants having a branched hydrocarbon group are used; they are selected from the phosphate surfactants of the formula (1), the sulfate surfactants of the formula (2) and the sulfonate surfactants of the formula (3).

In the formula (1), $R^1$ represents a hydrocarbon group having 5 to 13 carbon atoms. It preferably represents a linear or branched alkyl group. Preferable examples of such a linear alkyl group include hexyl, heptyl, octyl, nonyl, decyl, undecyl and dodecyl groups, while preferable examples of the branched alkyl group include 3-methylhexyl, 5-methylhexyl, 2-ethylhexyl, 5-methyloctyl, 3,5,5-trimethylhexyl and 3,7-dimethyloctyl groups. In particular, 3,5,5-trimethylhexyl and 3,7-dimethyloctyl groups each having two or more methyl groups in the side chain are preferable therefor.

In the formula (1), $R^2$ represents a hydrocarbon group having 5 to 11 carbon atoms. It preferably represents a linear or branched alkyl group. Preferable examples of such a linear alkyl group include pentyl, hexyl, heptyl, octyl and nonyl groups, while preferable examples of the branched alkyl group include 1-methylbutyl, 3-methylbutyl, 3-methylhexyl, 1,3,3-trimethylbutyl and 1,5-dimethylhexyl groups. In particular, 1,3,3-trimethylbutyl and 1,5-dimethylhexyl groups each having two or more methyl groups in the side chain are preferable therefor.

From the viewpoint of detergency and washing-off performance, $R^1$ and $R^2$ in the formula (1) are selected in such a manner as to control the sum of the carbon atoms therein to from 12 to 22, preferably from 12 to 20.

In the formula (1), $X^1$ and $X^2$ independently represent each a hydrogen atom, an alkali metal, ammonium, a basic amino acid residue or an alkanolamine residue carrying a hydroxyalkyl group having 2 to 3 carbon atoms. Examples of the alkali metal include lithium, sodium and potassium. Examples of the basic amino acid residue include arginine, lysine, histidine and ornithine residues. Examples of the alkanolamine residue include triethanolamine, diethanolamine and monoethanolamine residues.

In the sulfate-series surfactant of the formula (2), $R^3$ represents a branched hydrocarbon group having 6 to 24 carbon atoms. When $R^3$ is a linear hydrocarbon group, the penetrability of the detergent composition into stains tends to be lowered. When the carbon atom number of $R^3$ is excluded from the scope as defined above, there arises a tendency that the detergency and/or foaming power are deteriorated. It is preferable that $R^3$ is a branched alkyl group. Particular examples thereof include 2-hexyldecyl, 2-heptylundecyl, 2-octyldodecyl, 2-(1,3,3-trimethylbutyl)-5,7,7-tirmethyloctyl and 2-methyldecyl groups.

In the sulfate-series surfactant of the formula (2), M represents a hydrogen atom, an alkali metal, ammonium, a basic amino acid residue, an alkanolamine residue carrying a hydroxyalkyl group having 2 to 3 carbon atoms or an aliphatic alkanolammonium. Examples of the alkali metal include lithium, sodium and potassium. Examples of the basic amino acid residue include arginine, lysine, histidine and ornithine residues. Examples of the alkanolamine residue carrying a hydroxyalkyl group having 2 to 3 carbon atoms include triethanolamine, diethanolamine and monoethanolamine residues. Examples of the aliphatic alkanolammonium include 2-amino-2-methyl-1-propanol and 2-amino-2-methyl-1,3-propanediol.

In the formula (2), a is a number of from 0 to 10. When a is 0, a preferable sulfate-series surfactant of the formula (2) is a branched alkylsulfate compound. Preferable examples thereof include sodium 2-hexyldecylsulfate, sodium 2-(1,3,3-trimethylbutyl)-5,7,7-trimethyloctylsulfate and sodium 2-heptylundecylsulfate. When a is not 0, a preferable sulfate-series surfactant of the formula (2) is a branched alkylpolyoxyethylene sulfate compound. Preferable examples thereof include triethanolamine polyoxyethylene (2 or 4) 2-heptylundecylsulfate, triethanolamine polyoxyethylene (7) 2-octyldodecylsulfate and triethanolamine polyoxyethylene (4) 2-hexyldecylsulfate.

In the sulfonic acid-series surfactant of the formula (3), $R^4$ can be fundamentally defined in the same manner as the definition of $R^3$ of the formula (2). Similarly, M can be defined in the same manner as the definition of M in the formula (2). When $R^5$, which will be described hereinafter, is a hydrocarbon group, however, $R^4$ may be a linear hydrocarbon group. $R^5$ in Z represents a hydrogen atom or a hydrocarbon group having 10 to 14 carbon atoms, preferably a linear or branched alkyl group. When a hydrocarbon group is selected as $R^5$, the sum of the carbon atoms of $R^4$ and $R^5$ is controlled to from 6 to 24.

When Z is a group of the formula (4), a preferable sulfonic acid-series surfactant of the formula (3) is a branched alkylbenzenesulfonic acid compound. Particular examples thereof include sodium 2-octyldodecylbenzenesulfonate and sodium 2-heptylundecylbenzenesulfonate.

When Z is a group of the formula (5), a preferable sulfonic acid-series surfactant of the formula (3) is a branched alkylsulfonic acid compound. Particular examples thereof include sodium 1-octyldodecylsulfonate.

When Z is a group of the formula (6) or (7), a preferable sulfonic acid-series surfactant of the formula (3) is an α-olefinsulfonic acid compound. Particular examples thereof include sodium 2-hexyldeca-1-enesulfate.

When Z is a group of the formula (8), a preferable sulfonic acid-series surfactant of the formula (3) is a branched alkyloxyethylenesulfosuccinic acid compound. Particular examples thereof include sodium polyoxyethylene (3) 2-ethylhexylsulfosuccinate and sodium polyoxyethylene (1) 2-heptylundecylsulfosuccinate.

When Z is a group of the formula (9), a preferable sulfonic acid-series surfactant of the formula (3) is an α-sulfo branched fatty acid methyl ester compound. Particular examples thereof include sodium 1-methoxycarbonyltridecylsulfonate.

As the component (A), either one of these surfactants or a mixture thereof may be used. The content of the surfactant of the component (A) in the detergent composition preferably ranges from 1 to 30% by weight, still preferably from 1 to 20% by weight and particularly preferably from 1 to 10% by weight. A high detergency can be achieved by using the component (A) in an amount falling within this range.

In the present invention, said component (A) is combined with a component (B), at least one nonionic surfactant. Any types of known nonionic surfactants can be used. In particular, those nonionic surfactant having 1 to 50 moles, on average, of a polyoxyalkylene group added thereto per hydrophobic group or a less irritative sugar-series nonionic surfactant are preferable.

In the nonionic surfactant having 1 to 50 moles, on average, of a polyoxyalkylene group added thereto per hydrophobic group, the number of moles of the polyoxyalkylene group added per hydrophobic group in the nonionic surfactant ranges from 1 to 50 moles, preferably from 3 to 15 moles, on average. When this number of moles exceeds 50 moles, the detergency is deteriorated. When no polyoxyalkylene group is added, on the other hand, only an extremely insufficient surface activity can be achieved.

Examples of the nonionic surfactant to be used as the component (B) include (B1) polyoxyalkylene alkyl ethers, (B2) polyoxyalkylene fatty acid esters, (B3) polyoxyalkylene sorbitan fatty acid esters, (B4) polyoxyalkylene sorbitol fatty acid esters, (B5) polyoxyalkylene glycerol fatty acid esters, (B6) polyoxyalkylene alkylamines, (B7) polyoxyalkylene alkyl fatty acid amides and (B8) polyoxyalkylene alkylphenyl formaldehyde condensates. As examples of the polyoxyalkylene group to be used herein, polyoxyethylene and polyoxypropylene groups and a combination thereof may be cited.

Preferable examples of the nonionic surfactants (B1) to (B8) having polyoxyethylene (hereinafter referred to simply as POE) or polyoxypropylene (hereinafter referred to simply as POP) group added thereto are as follows.

(B1) Polyoxyalkylene ether

POE sec-alkyl (12–14) ether, POE lauryl ether, POE cetyl ether, POE oleyl ether, POE stearyl ether, POE nonylphenyl ether, POE octylphenyl ether, POE hexyldecyl ether, POE isostearyl ether, POE octyldodecyl ether, POE decylpentadecyl ether, POE behenyl ether, POE decyltetradecyl ether, POE cholesteryl ether, POE higher alcohol ether, POE POP stearyl ether, POE POP cetyl ether, POE POP decyltetradecyl ether, POE POP butyl ether, POE POP hexylglycol ether, POE POP pentaerythritol ether, POE POP lauryl ether, etc.

(B2) POE fatty acid ester

POE monolaurate, POE monopalmitate, polyoxyethylene monooleate, POE monostearate, POE dilaurate, POE distearate, POE tristearate, POE dioleate, POE trioleate, POE trimyristate, POE hardened castor oil, POE castor oil, etc.

(B3) POE sorbitan fatty acid ester

POE sorbitan monolaurate, POE sorbitan monopalmitate, POE sorbitan monooleate, POE sorbitan monostearate, POE sorbitan trioleate, POE sorbitan tristearate, POE sorbitan sesquioleate, etc.

(B4) POE sorbitol fatty acid ester

POE sorbitol tetraoleate, POE sorbitol monolaurate, etc.

(B5) POE glycerol fatty acid ester

POE glycerol monooleate, POE glycerol monostearate, POE glycerol vegetable oil fatty acid ester, POE glycerol animal fanimal fat fatty acid ester, etc.

(B6) POE amine

POE stearylamine, POE oleylamine, etc.

(B7) POE fatty acid amide

POE stearamide, POE oleamide, etc.

(B8) POE alkylphenyl formaldehyde condensate

POE nonylphenyl formaldehyde, etc.

The number of the hydrophobic groups in the nonionic surfactant of the component (B) differs from surfactant to surfactant. For example, a POE alkyl ether has one hydrophobic group, a POE sorbitan monofatty acid has one hydrophobic group, a POE sorbitan difatty acid has two hydrophobic groups and POE hardened castor oil has three hydrophobic groups.

Preferable examples of the sugar-series nonionic surfactant include alkylsaccharide-series surfactants, sugar amide-series surfactants and sucrose fatty acid ester-series surfactants. Among all, alkylsaccharide-series surfactants are particularly preferable therefor.

As an alkylsaccharide-series surfactant, it is preferable to use, for example, a compound represented by the formula (10)

$$R^6-O-(R^7O)_aG_b \quad (10)$$

wherein $R^6$ represents a linear or branched alkyl, alkenyl or alkylphenyl group having 6 to 18 carbon atoms, $R^7$ represents an alkylene group having 2 to 4 carbon atoms, G represents a reducing sugar having 5 to 6 carbon atoms, a is a number of from 0 to 10 and b is a number of from 1 to 10.

From the viewpoint of improving the cleansing performance (foaming power, etc.) of the detergent composition, preferable examples of $R^6$ in the formula (10) include linear or branched alkyl, alkenyl or alkylphenyl group having 6 to 18 carbon atoms, still preferably linear or branched alkyl groups having 8 to 14 carbon atoms. Particular examples thereof include octyl, nonyl, decyl, undecyl, dodecyl, tridecyl and tetradecyl groups. Among all, decyl, dodecyl and tetradecyl groups are particularly preferable therefor.

From the viewpoint of improving the cleansing performance (foaming power, etc.) of the detergent composition, it is preferable that a, which stands for the number of the repeat of $(R^7O)$ (i.e., the average degree of polymerization), ranges from 0 to 10, still preferably from 0 to 3 and particularly preferably 0.

Preferable examples of the saccharide moiety G include reducing sugars having 5 to 6 carbon atoms, in particular, glucose, galactose and fructose. It is preferable that b, which stands for the number of the repeat of G (i.e., the average degree of polymerization), ranges from 1 to 10, still preferably from 1 to 4 and particularly preferably from 1 to 1.4. From the viewpoint of detergency, it is preferable that an alkylsaccharide-series surfactant, wherein b is a number of from 1 to 4, is contained in an amount of 80% or more based on the total alkyl saccharide-series surfactants of the formula (10).

The degree of hydrophobicity of $R^6$ would be elevated with an increase in the number of the carbon atoms in $R^6$. It is therefore preferable to elevate the value b so as to offset the elevated hydrophobicity. That is to say, b preferably ranges from 1 to 1.4 when $R^6$ has 8 to 11 carbon atoms, while b preferably ranges from 1.5 to 4 when $R^6$ has 12 to 14 carbon atoms.

As a preferable example of the sugar amide-series surfactant, use can be made of a compound represented by the formula (11):

$$R^8-CO-NR^9X^3 \quad (11)$$

wherein $R^8$ represents a linear or branched alkyl, alkenyl or alkylphenyl group having 5 to 17 carbon atoms, $R^9$ represents a hydrogen atom, a linear or branched alkyl or alkenyl group having 1 to 18 carbon atoms, $-(CH_2CH(R^{10})O)_c-$H, wherein $R^{10}$ represents a hydrogen atom or a methyl group and c is a number of from 0 to 10, $-CH_2CH_2OH$, $-CH_2CH(OH)CH_3$ or $-CH_2CH_2CH_2OH$, and $X^3$ represents a polyhydroxyalkyl group comprising a sugar residue having 4 to 30 carbon atoms.

Examples of $R^8$ in the formula (11) include linear or branched alkyl, alkenyl and alkylphenyl groups having 5 to 17 carbon atoms. In particular, examples of $R^8CO$ include groups derived from captic acid, caprylic acid, lauric acid, myristic acid, palmitic acid, stearic acid and isostearic acid. Among all, groups derived from capric acid and lauric acid are particularly preferable therefor.

Preferable examples of $R^9$ include a hydrogen atom and methyl, ethyl, n-propyl, isopropyl, n-butyl, t-butyl, n-hexyl, octyl, 2-ethylhexyl, decyl, dodecyl, stearyl and isostearyl groups, polyethylene glycol and polypropylene glycol groups of a degree of polymerization of from 2 to 10, and 2-hydroxyethyl, 2-hydroxyproypl and 3-hydroxypropyl groups. Among all, a hydrogen atom and methyl, ethyl, 2-hydroxyethyl, 2-hydroxypropyl and 3-hydroxypropyl groups are particularly preferable therefor.

The polyhydroxyalkyl group comprising a sugar residue having 4 to 30 carbon atoms represented by $X^3$ involves polyhydroxyalkyl groups having 4 to 7 carbon atoms and binding to a mono-, di- or oligosaccharide group via a glycoside bond.

As a sucrose fatty acid ester-series surfactant, it is preferable to use a compound represented by the formula (12):

(12)

wherein $R^{11}$, $R^{12}$ and $R^{13}$ independently represent each a hydrogen atom or a linear or branched, saturated or unsaturated acyl group having 8 to 24 carbon atoms, provided that $R^{11}$, $R^{12}$ and $R^{13}$ do not represent hydrogen atoms at the same time. In general, it is a mixture of mono-, di- and tri-acylated compounds. In this case, it is preferable that the weight ratio of (monoacylated compound)/(diacylated compound+triacylated compound) ranges from 70/30 to 30/70.

In the formula (12), it is preferable that $R^{11}$, $R^{12}$ and $R^{13}$ represent each an acyl group having 10 to 18 carbon atoms, in particular, a lauroyl, myristoyl or palmitoyl group, among the acyl groups having 8 to 24 carbon atoms.

As the component (B), use can be made of either one of the nonionic surfactants having 1 to 50 moles, on average, of a polyoxyalkylene group added thereto per hydrophobic group and the less irritative sugar-series nonionic surfactants or a combination thereof. When the component (B) is contained in the detergent composition in an excessively small amount, no sufficient detergency can be achieved. When it is contained in an excessively large amount, on the other hand, the porous membrane of the foamer container frequently undergoes jamming. Thus, it is preferably that the content of the component (B) in the detergent composition ranges from 0.5 to 30% by weight, still preferably from 1 to 30% by weight.

In a preferable skin cleanser, the total content of the components (A) and (B) in the detergent composition is from 3 to 30% by weight.

It is preferable that the detergent composition to be used in the present invention further contains a polyol as the component (C).

Examples of the polyol to be used as the component (C) include propylene glycol, 1,3-butylene glycol, glycerol, sorbitol, maltitol, xylitol, glucose, polyethylene glycol 400, polyethylene glycol 600, dipropylene glycol, diglycerol, 1,3-propylene glycol, hexylene glycol, sucrose and polyoxyethylene glycoside derivatives.

Either one of these polyols or a combination thereof may be used as the component (C). The content of the polyol of the component (C) in the detergent composition preferably ranges from 3 to 30% by weight, still preferably from 5 to 30% by weight. A detergent composition containing the polyol as the component (C) in a content falling within this range can impart a good texture to the skin during massage with the foam of the composition and, moreover, make the skin moist after washing off the detergent composition.

It is preferable that the detergent composition to be used in the present invention further contains ethanol as the component (D). The content of the ethanol of the component (D) in the detergent composition preferably ranges from 0.1 to 10% by weight, still preferably from 1 to 5% by weight. A detergent composition containing ethanol as the component (D) in a content falling within this range can give creamy foam and achieve an improved detergency. In addition to the surfactants of the components (A) and (B), the detergent composition to be used in the skin cleanser of the present invention may further contain other surfactants, if required. Examples of such surfactants include anionic surfactants such as higher fatty acid salts, mono-linear alkylphosphate salts, linear alkylbenzenesulfonates and acylated amino acid salts; ampholytic surfactants such as carbobetaine-series, sulfobetaine-series, imidazoliniumbetaine-series and amidobetaine-series surfactants; cationic surfactants such as mono- or di-alkyl-added quaternary ammonium salts having linear or branched alkyl group(s) to which alkylene oxide(s) are optionally added; and nonionic surfactants such as polyoxyalkylene-series, polyglycerol fatty acid ester-series, polyhydric alcohol fatty acid ester-series, fatty acid diethanolamide-series and trialkylamine oxide-series surfactants.

Particularly preferable examples of the ampholytic surfactants include hydroxypropylsulfobetaine and desalted secondary imidazoliniumbetaine. Preferable examples of the anionic surfactants include alkali metal, alkaline earth metal, alkanolamine and basic amino acid salts of fatty acids having 8 to 22 carbon atoms. Particularly preferable examples of the cationic surfactants include linear monoalkyl quaternary ammonium salts having 12 to 16 carbon atoms and quaternary ammonium salts carrying a branched alkyl group having 20 to 28 carbon atoms. Preferable examples of the nonionic surfactants include fatty acid diethanolamides carrying an alkyl group having 8 to 22 carbon atoms, dimethylamine oxides carrying a secondary alkyl group having 12 to 14 carbon atoms and polyoxyethylene alkyl ethers carrying a secondary alkyl group having 12 to 14 carbon atoms. Either one of these ampholytic surfactants, anionic surfactants, cationic surfactants and nonionic surfactants or a combination thereof may be used. The content of the surfactant(s) in the detergent composition preferably ranges from 0.5 to 30% by weight, still preferably from 1 to 20% by weight.

When the detergent composition to be used in the skin cleanser of the present invention has an excessively high viscosity, it hardly passes through a porous membrane and, in its turn, scarcely gives any creamy foam. Accordingly, it is preferable to regulate the viscosity of the detergent composition to 1 to 100 cps, still preferably 1 to 50 cps, at If necessary, the detergent composition to be used in the skin cleanser of the present invention may further contain other components commonly employed in detergent compositions, so long as the effects of the present invention are not deteriorated thereby. Examples of these additional components include lanolin and its derivatives, esters such as isopropyl myristate, oily components such coconut oil triglycerides, humectants such as polyglycerol fatty acid esters, bactericides such as triclosan and trichlorocarbanilide, anti-inflammatory agents such as dipotassium glycyrrhetinate and tocopherol acetate, antidandruff agents such as zinc pyrithione and octopirox, preservatives such as methylparaben and butylparaben, chelating agents such as ethylenediaminetetraacetic acid or its salts and hydroxyethanediphosphonic acid or its salts, pH regulating agents such as citric acid and succinic acid, salts such as sodium chloride, pearling agents, perfumes, coloring matters, UV absorbers and antioxidants.

The detergent composition of the present invention can be produced by mixing the above-mentioned components in a conventional manner.

The skin cleanser of the present invention consists of the detergent composition as described above which is packed in a foamer container. As the foamer container, use is made of one provided with a porous membrane. Thus creamy foam can be formed and a good feel in use can be achieved in cleansing the skin with the skin cleanser. Examples of the porous membrane include sponge, sintered materials and nets. A thin net is preferable therefor among these porous membranes. This is because, when the detergent composition adhering and remaining on the membrane is dried and solidified and thus causes jamming, the solidified matter can be easily dissolved in the foam flow subsequently discharged from the container, thus solving the problem of jamming. In such a case, it is preferable to use a net of 50 to 500 mesh, still preferably 150 to 400 mesh. By using a net of a mesh size falling within this range, creamy foam with excellent massage performance can be formed. Preferable examples of the material of the net include nylon and polyester.

It is preferable that the container to be used in the skin cleanser of the present invention is provided with at least one, still preferably two or more, porous membranes as defined above. From the viewpoints of cost, foaming stability, etc., it is still preferable that the container has two membranes.

The foamer container may be an arbitrary one, so long as a definite amount of the detergent composition can be mixed with a definite amount of air thereby and discharged therefrom in the state of foam. Examples thereof include squeeze foamers composed of a soft container to be pushed with fingers, for example, those described in JP-A-U-58-174272, JP-A-U-62-42787 and JP-B-52-16567, and pump foamers provided with a pumping unit with a cap which is to be pushed with fingers, for example, those described in JP-A-U-3-7963 and JP-A-U-62-103458 (the term "JP-A-U" as used herein means an "unexamined published Japanese utility model application"). A preferable example thereof is a foamer container shown by FIG. 1.

Figure 1:
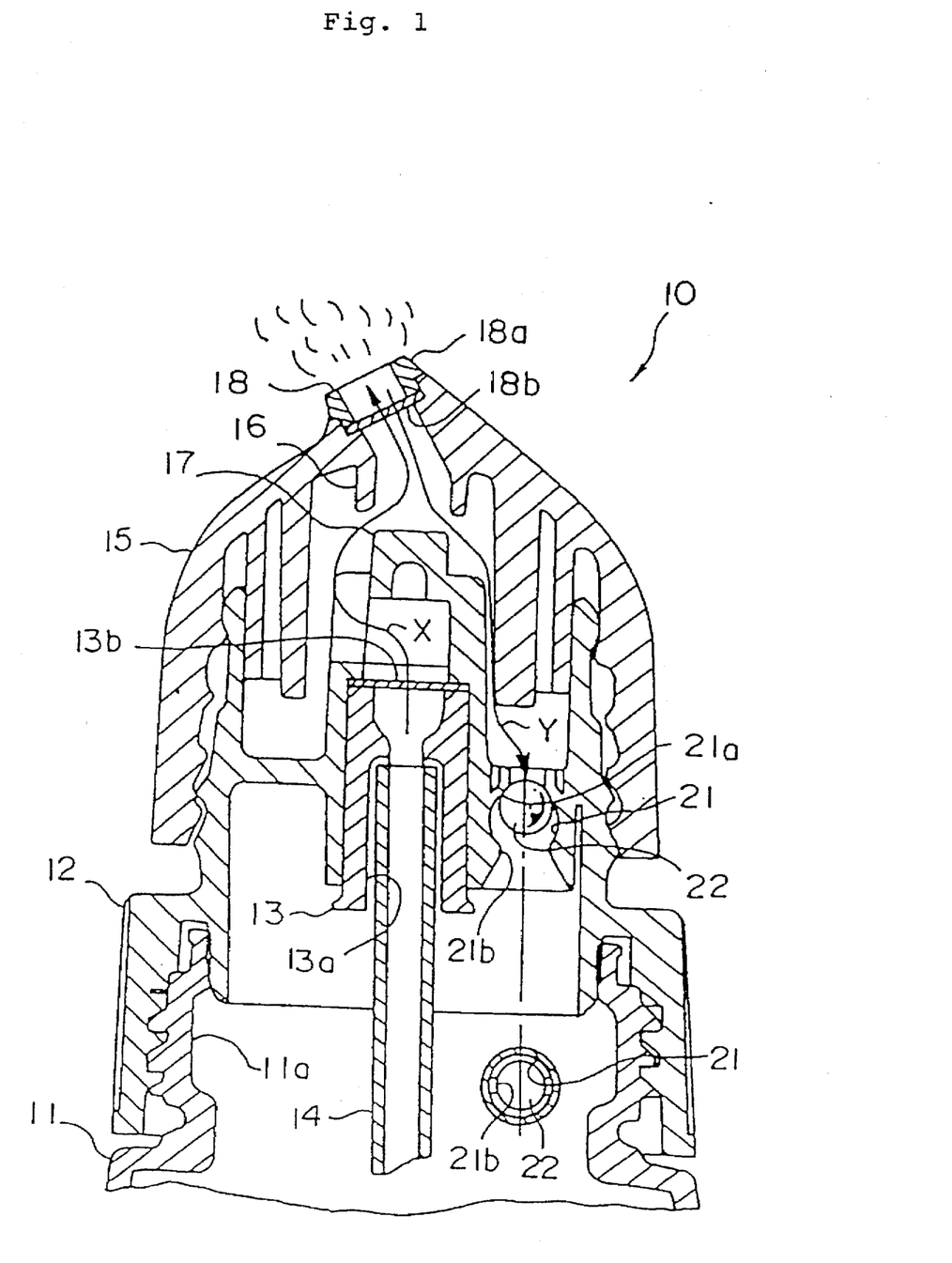
FIG. 1 is a partially enlarged sectional view of a foamer container wherein each symbol has the meaning as defined below.

In the foamer container 10 of FIG. 1, the squeezable body 11 of the container has an opening 11a provided with a screw cap 12. A gas/liquid mixing unit 13 is located at the center of the inside of the cap 12. This gas/liquid mixing unit 13 is provided with a tube connector 13a and a porous membrane 13b.

Into the foamer container 10, a dip tube 14 is fitted via a definite space from the tube connector 13a of the gas/liquid mixing unit 13. Thus the dip tube 14 is supported by the cap 12 and inserted into the container body 11 while being linked to the gas/liquid mixing unit 13. The foamer container 10 has a switch nozzle 15 screwed on the discharge side (upper part in the figure) of the gas/liquid mixing unit 13 of the cap 12. This nozzle 15 is switched from on to off and vice versa by rotating at an angle of 90° against the cap 12. When the nozzle 15 is set at "off", a seal ring 16 circularly projecting from the nozzle 15 closely adheres to a plug 17 located above the gas/liquid mixing unit 13. When the nozzle 15 is set at "on", the seal ring 16 is separated from the plug 17 so as to form a discharge channel. A discharge port 18 of the nozzle 15 is provided with a porous membrane fixing member 18a and a porous membrane 18b at the tip. The porous membrane 18b is fixed by the porous membrane fixing member 18a.

The foamer container 10 has a ball valve 22 in the air-return channel 21 of the cap 12. At the discharge of foam, this ball valve 22 closely adheres to a sealing unit 21a located at the upper part of the air-return channel 21 and thus elevate the pressure in the container body 11 via squeezing.

After the completion of the discharge of the foam, the ball valve 22 is held by a project 21b located in the lower part of the air-return channel 21. After relieving the squeezing, external air is introduced into the container body 11 due to the negative pressure in the container caused by the restoring force of the container body 11.

Foam is discharged from the foamer container 10 as follows. (1) By rotating the nozzle 15, the seal ring 16 of the nozzle 15 is separated from the plug 17 of the cap 12 to thereby form a foam discharge channel shown by an arrow X in FIG. 1. (2) When the container body 11 is manually squeezed, the air (or liquid) directly introduced into the gas/liquid mixing unit 13 of the cap 12 is mixed with the liquid (or air) introduced into the gas/liquid mixing unit 13 via the dip tube 14. Then the resulting mixture is allowed to pass through the porous membrane 13b to thereby give foam. Next, the foam is transferred along the above-mentioned foam discharge channel X and discharged from the discharge port 18 via the porous membrane 18b provided at the tip of the discharge port 18 of the nozzle 15. Then the ball valve 22 closely adheres to the sealing unit 21a of the air-return channel 22 to thereby elevate the pressure in the container body 11.

(3) After the completion of the discharge of the foam, the ball valve 22 is held by the project 21b located in the air-return channel 21. After relieving the squeezing, the external air is introduced into the container body 11 along the air-return channel shown by an arrow Y in FIG. 1 due to the negative pressure in the container caused by the restoring force of the container body 11. Although the external air tries to advance in the foam discharge channel X in the opposite direction too, it is prevented by the foam remaining on the porous membrane 13b. Thus the air advances along the air-return channel Y as described above. When the foam remaining on the porous membrane 18b allows only slow introduction of the air into the air-return channel Y, the air-return channel 21 and a ball valve 22 may be located at such positions as to directly link to the outside of the cap 12.

In the skin cleanser of the present invention, the detergent composition is converted into foam after passing trough a membrane. The density of the foam thus formed preferably ranges from 0.03 to 0.25 g/ml. A foam density falling within this range can give a high detergency and a good massage. The foam density can be determined by discharging the foam from the foamer container into a 100 ml graduated cylinder and weighing.

The skin cleanser of the present invention can be appropriately used as face cleansing foams, cleansing foams, makeup removing foams, shaving foams, shampoos and body cleansing foams. Also, it is applicable to kitchen detergents.

In the skin cleanser of the present invention, a detergent composition is prepared from a specific anionic surfactant and a specific sugar-series nonionic surfactant and then packed in a foamer container provided with a porous membrane. The foam discharged from this foamer container via the porous membrane has a high detergency, a uniform and low density and a creamy texture. Moreover, the foam is excellent in shape retention. With the use of this foam, therefore, a good massage can be easily effected and stains, which are hardly removable, can be fully washed off while giving a good feel in use.

To further illustrate the present invention in greater detail, the following Examples will be given.

EXAMPLES 1 TO 3 AND COMPARATIVE EXAMPLES 1 TO 3

The components of the compositions shown in Tables 1A and 1B were homogeneously mixed to thereby give each detergent composition. Then the detergent composition was packed in a squeeze foamer container shown in FIG. 1 to thereby give a skin cleanser. The skin cleanser was discharged in the form of foam which was then evaluated by 10 skilled panelists in foam qualities and detergency by the methods as will be described hereinbelow. Table 1 summarizes the results.

In the following tables, TEA means triethanolamine residue, POE means polyoxyethylene residue and POP means polyoxypropylene residue.

Method for evaluating detergency

A lipstick was applied onto the forearm at a ratio of 10 mg/5 cm$^2$. After massaging with 0.1 g of foam discharged from the skin cleanser for 30 seconds, the forearm was washed with running water. Then the amount of the lipstick remaining on the skin of the forearm was evaluated with the naked eye in accordance with the following criteria.

Criteria for evaluating detergency

| Rank | State |
| --- | --- |
| ○: | almost completely washed off. |
| △: | almost washed off. |
| ×: | scarcely washed off. |

Method for evaluating foam qualities 1.0 g of foam was discharged from the skin cleanser onto the palm of the hand and the qualities of the foam were evaluated with the naked eye in accordance with the following criteria.

Criteria for evaluating foam qualities

| Rank | State |
| --- | --- |
| ○: | fine and stable foam. |
| △: | coarse and unstable foam. |
| ×: | not foaming. |

TABLE 1A

| | (wt. %) | | | | | |
| --- | --- | --- | --- | --- | --- | --- |
| | Example | | | Comp. Example | | |
| Component | 1A | 2A | 3A | 1A | 2A | 3A |
| TEA 2-hexyldecylphosphate | 5 | — | 10 | — | — | 15 |
| TEA 2-hexyldecylsulfate | — | 5 | — | 10 | — | — |
| arginine 2-heptylundecyl-phosphate | 5 | 5 | — | 5 | — | — |
| POE(20) sorbitan monostearate | 5 | 5 | — | — | 5 | — |
| POE(9)-sec-alkyl (C$_{12-14}$) ether | — | — | 5 | — | 10 | — |
| glycerol | 10 | 10 | 10 | 10 | 10 | 10 |
| 1,3-butylene glycol | 10 | 10 | 10 | 10 | 10 | 10 |
| ethanol | 5 | 5 | 5 | 5 | 5 | 5 |
| purified water | 60 | 60 | 60 | 60 | 60 | 60 |
| (Evaluation) | | | | | | |
| detergency | ○ | ○ | ○ | △ | △ | △ |
| foam qualities | ○ | ○ | ○ | ○ | × | ○ |

The results given in Table 1A indicate that the skin cleansers of Examples showed each a high detergency and very excellent foam qualities. In contrast, the skin cleansers of Comparative Examples 1A and 3A showed each an insufficient detergency due to the lack of the surfactant of the component (B). The skin cleanser of the Comparative Example 2A was unsatisfactory not only in detergency but also in foam qualities due to the lack of the surfactant of the component (A).

TABLE 1B

| | (wt. %) | | | | | |
| --- | --- | --- | --- | --- | --- | --- |
| | Example | | | Comp. Example | | |
| Component | 1B | 2B | 3B | 1B | 2B | 3B |
| arginine 2-hexyldecyl-phosphate | 5 | — | — | 15 | — | — |
| TEA 2-(1,3,3-trimethyl-butyl)-5,7,7-trimethyloctyl-phosphate | — | 5 | — | — | 10 | — |
| TEA 5,7,7-trimethyloctyl-phosphate | | | | | | |
| sodium POE(4) 2-hexyldecyl-sulfate | | | 5 | — | 5 | |
| alkylsaccharide of formula (10) (R$^6$ = C$_{12}$H$_{25}$, a = 0, G = glucose, b = 1.3) | 10 | 5 | 10 | — | — | 10 |
| alkylsaccharide of formula (10) (R$^6$ = C$_{18}$H$_{37}$, a = 0, G = glucose, b = 2) | — | 5 | — | — | — | 5 |
| glycerol | 10 | 10 | 10 | 10 | 10 | 10 |
| ethanol | 3 | 3 | 3 | 3 | 3 | 3 |
| purified water | 72 | 72 | 72 | 72 | 72 | 72 |
| (Evaluation) | | | | | | |
| detergency | ○ | ○ | ○ | △ | △ | △ |
| foam qualities | ○ | ○ | ○ | △ | △ | × |

The results given in Table 1B indicate that the skin cleansers of Examples were excellent in detergency and foam qualities. In contrast, the skin cleansers of Comparative Examples were insufficient both in detergency and foam qualities due to the lack of the surfactants of the components (A) and (B).

EXAMPLE 4

The procedure of Example 1 was repeated but using the components of the compositions as specified in Tables 2A and 2B to thereby produce skin cleansers for removing makeup. Ten skilled panelists were employed and a waterproof foundation was applied onto the forearm of each panelist at a ratio of 5 mg/5 cm$^2$. After washing the forearm with 0.1 g of foam discharged from the skin cleanser for 30 seconds, the amount of the foundation remaining on the skin of the forearm was evaluated with the naked eye. As a result, the foundation could be almost completely washed off and scarcely remained.

TABLE 2A

| Component | wt. % |
| --- | --- |
| potassium 2-hexyldecylphosphate | 2 |
| TEA 2-(1,3,3-trimethylbutyl)-5,7,7-trimethyl-octylphosphate | 2 |
| TEA POE(4) 2-octyldodecylsulfate | 2 |
| POE(6) coconut oil fatty acid sorbitan | 3 |
| POE(20) octyl dodecyl ether | 1 |
| polyethylene glycol 600 monolaurate | 5 |
| propylene glycol | 10 |
| glycerol | 10 |
| ethanol | 5 |
| citric acid | 1 |
| L-arginine | 1 |
| edetic acid | 0.1 |
| methylparaben | 0.1 |

TABLE 2A-continued

| Component | wt. % |
| --- | --- |
| ethylparaben | 0.1 |
| dibutylhydroxytoluene | 0.1 |
| perfume | trace |
| purified water | the balance |

TABLE 2B

| Component | wt. % |
| --- | --- |
| TEA 2-hexyldecylsulfate | 3.0 |
| TEA heptylundecylphosphate | 2.0 |
| alkylsaccharide of formula (10) ($R^6 = C_{12}H_{25}$, a = 0, G = glucose, b = 2) | 10.0 |
| TEA laurate | 3.0 |
| TEA myristate | 2.0 |
| POE(3)-sec-alkyl ($C_{12-14}$) ether | 3.0 |
| lauroyldiethanolamide | 3.0 |
| sorbitan laurate | 0.5 |
| 1,3-butylene glycol | 5.0 |
| ethanol | 2.0 |
| $Na_2SO_3$ | 0.5 |
| BHT | 0.2 |
| methylparaben | 0.1 |
| propylparaben | 0.1 |
| hydroxyethanediphosphonic acid | 0.1 |
| perfume | trace |
| purified water | the balance |

EXAMPLE 5

The procedure of Example 1 was repeated but using the components of the compositions as specified in Tables 3A and 3B to thereby produce skin cleansers for cleansing body. Ten skilled panelists were employed and each washed the body with foam discharged from the skin cleanser. As a result, stains on the body could be almost completely washed off.

TABLE 3A

| Component | wt. % |
| --- | --- |
| TEA POE(7) 2-octyldodecylsulfate | 5 |
| POE(15) isostearyl ether | 3 |
| POE(3) POP(17) glycol | 3 |
| polyethylene glycol monostearate (EO15) | 1 |
| propylene glycol | 10 |
| isoprene glycol | 10 |
| ethanol | 5 |
| Triclosan | 0.1 |
| 1-menthol | 0.05 |
| lauryldimethylamine oxide | 1 |
| dibutylhydroxytoluene | 0.1 |
| perfume | trace |
| purified water | the balance |

TABLE 3B

| Component | wt. % |
| --- | --- |
| potassium 2-hexyldecylphosphate | 3.0 |
| sodium POE(3) 2-ethylhexylsulfosuccinate | 5.0 |
| sucrose monolaurate | 5.0 |
| TEA laurate | 3.0 |
| potassium dodecylphosphate | 5.0 |
| POE(15) isostearyl ether | 2.0 |
| POE(3) POP(17) glycol | 2.0 |
| propylene glycol | 5.0 |

TABLE 3B-continued

| Component | wt. % |
| --- | --- |
| hexylene glycol | 5.0 |
| ethanol | 3.0 |
| Triclosan | 0.5 |
| 1-menthol | 0.5 |
| citric acid | 1.0 |
| lauryldimethylamine oxide | 1.0 |
| BHT | 0.1 |
| perfume, coloring matter | trace |
| purified water | the balance |

EXAMPLE 6

The procedure of Example 1 was repeated but using the components of the compositions as specified in Tables 4A and 4B to thereby produce skin cleansers for cleansing the face. Ten skilled panelists were employed and each massaged the forearm, onto which 10 mg/5 cm² of a model sebum had been applied, with 0.1 g of foam discharged from the skin cleanser for 30 seconds. Then the amount of the model sebum remaining on the skin of the forearm was evaluated with the naked eye. As a result, the model sebum could be almost completely washed off.

TABLE 4A

| Component | wt. % |
| --- | --- |
| arginine 2-hexyldecylphosphate | 3 |
| sodium 1-octyldecylsulfonate | 3 |
| lauryl polyglycoside | 5 |
| POE(20) sorbitan monolaurate | 2 |
| POE(20) sorbitan isostearate | 2 |
| polyethylene glycol monooleate (10EO) | 2 |
| diethanolamide laurate | 2 |
| glyceryl caprate | 1 |
| 1,3-propylene glycol | 10 |
| glycerol | 10 |
| ethanol | 3 |
| macadamia nut oil | 0.1 |
| methylparaben | 0.1 |
| propylparaben | 0.1 |
| hydroxyethanediphosphonic acid | 0.1 |
| dipotassium glycyrrhetinate | 0.1 |
| perfume | trace |
| purified water | the balance |

TABLE 4B

| Component | wt. % |
| --- | --- |
| TEA POE(7) octyldodecylsulfate | 5.0 |
| TEA 2-hexyldecylphosphate | 5.0 |
| sugar amide of formula (11) ($R^8CO$ = lauroyl, $R^9$ = H, X = glucose residue) | 8.0 |
| TEA myristate | 2.0 |
| TEA monoalurylphosphate | 5.0 |
| N-lauryl β-alanine sodium | 3.0 |
| POE(3) tetradecyl ether | 0.5 |
| diglyceryl isostearate | 0.5 |
| propylene glycol | 5.0 |
| ethanol | 2.0 |
| BHT | 0.1 |
| macadamia nut oil | 0.1 |
| edetic acid | 0.1 |
| dipotassium glycyrrhetinate | 0.1 |
| perfume | trace |
| purified water | the balance |

EXAMPLE 7

The procedure of Example 1 was repeated but using the components of the compositions as specified in Tables 5A and 5B to thereby produce skin cleansers for shampooing. Ten skilled panelists were employed and each washed the hair, which had been set with the use of 0.1 g of a polymer-based aerosol hair setting agent, with 3 g of foam discharged from the skin cleanser. As a result, the hair setting agent could be almost completely washed off.

TABLE 5A

| Component | wt. % |
|---|---|
| sodium 2-hexyldecylsulfate | 3 |
| sodium POE(4) 2-hexyldecylsulfate | 2 |
| sodium POE(4) 2-ethylhexylsulfosuccinate | 2 |
| POE(3)-sec-alkyl (C$_{12-14}$) ether | 5 |
| POE(10) octyl phenyl ether | 3 |
| POE(9) nonyl phenyl ether | 3 |
| coconut oil fatty acid diethanolamide | 1 |
| lauric acid amide propylbetaine | 1 |
| lauroylmethyltaurin sodium | 1 |
| propylene glycol | 10 |
| ethanol | 5 |
| methylparaben | 0.1 |
| succinic acid | 1 |
| perfume, coloring matter | trace |
| purified water | the balance |

TABLE 5B

| Component | wt. % |
|---|---|
| TEA 2-hexyldecylsulfate | 3.0 |
| sodium POE(4) 2-hexyldecylsulfate | 10.0 |
| sodium 1-octyldecylsulfonate | 2.0 |
| alkylsaccharide of formula (10) (R$^6$ =C$_{12}$H$_{25}$, a = 0, G = glucose, b = 1.5) | 5.0 |
| coconut oil fatty acid diethanolamide | 1.0 |
| glyceryl caprate | 0.5 |
| lauric acid amide propylbetaine | 1.0 |
| lauroylmethyltaurin sodium | 0.5 |
| POE(20) sorbitan monolaurate | 1.0 |
| ethanol | 3.0 |
| propylene glycol | 5.0 |
| methylparaben | 0.1 |
| perfume, coloring matter | trace |
| purified water | the balance |

COMPARATIVE EXAMPLES 4 TO 10

The skin cleansers employed in the above Examples 1 to 7 were used without packing in a foamer container. As a result, each skin cleanser showed an insufficient foaming power and easily ran out of the skin. Thus, no sufficient detergency could be achieved thereby.

The skin cleanser of the present invention can give less irritative, uniform and creamy foam with a high detergency. By using the foam, oily stains which are hardly removed (for example, cosmetics such as lipstick, eye-makeup, waterproof foundation, etc.) can be thoroughly washed off while giving a good feel in use.

While the invention has been described in detail and with reference to specific embodiments thereof, it will be apparent to one skilled in the art that various changes and modifications can be made therein without departing from the spirit and scope thereof.

What is claimed is:

1. A skin cleanser comprising a detergent composition which contains the following components (A) and (B) packed in a foamer container provided with a porous membrane:

(A) 1 to 30% by weight of at least one anionic surfactant having a branched hydrocarbon group selected from phosphate surfactants represented by the formula (1), sulfate surfactants represented by the formula (2) and sulfonate surfactants represented by the formula (3):

$$R^1R^2CHCH_2OP(=O)(OX^1)(OX^2) \quad (1)$$

$$(R^3—(Y)_a—OSO_3^-)_n(M^{n+}) \quad (2)$$

$$(R^4—(Z)—SO_3^-)_nM^{n+} \quad (3)$$

wherein, in the formula (1), $R^1$ represents a hydrocarbon group having 5 to 13 carbon atoms and $R^2$ represents a hydrocarbon group having 5 to 11 carbon atoms, provided that the sum of the carbon atoms in $R^1$ and $R^2$ is from 12 to 22, and $X^1$ and $X^2$ independently represent a hydrogen atom, an alkali metal, ammonium, a basic amino acid residue or an alkanolamine residue carrying a hydroxyalkyl group having 2 to 3 carbon atoms; and in the formulae (2) and (3), $R^3$ represents a branched hydrocarbon group having 6 to 24 carbon atoms, Y represents an oxyethylene group, a is a number of from 0 to 10, $R^4$ represents a branched or a linear hydrocarbon group having 6 to 24 carbon atoms, Z is a group represented by any of the following formulae (4) to (9):

$$—CHR^5—(CH_2)_b—C_6H_4— \quad (4)$$

$$—CHR^5— \quad (5)$$

$$—CH=CH—(CH_2)_b— \quad (6)$$

$$—CH(OH)—(CH_2)_b— \quad (7)$$

$$—O—(CH_2CH_2O)_b—COCH_2CH(COOH)— \quad (8)$$

$$—CH(COOCH_3)— \quad (9)$$

wherein, in the formulae (4) to (9), $R^5$ represents a hydrogen atom or a hydrocarbon group having 10 to 14 carbon atoms and b is a number of from 0 to 10; M represents a hydrogen atom, an alkali metal, ammonium, a basic amino acid residue, an alkanolamine residue carrying a hydroxyalkyl group having 2 to 3 carbon atoms or an aliphatic alkanolammonium and n is the valence of M;

(B) 0.5–30% by weight of at least one nonionic surfactant.

2. A skin cleanser as claimed in claim 1, wherein said detergent composition comprises said component (A) and said component (B) in a total amount of from 3 to 30% by weight.

3. A skin cleanser as claimed in claim 1, wherein said detergent composition further comprises (C) from 3 to 30% by weight of a polyol.

4. A skin cleanser as claimed in claim 1, wherein said detergent composition further comprises (D) from 0.1 to 10% by weight of ethanol.

5. A skin cleanser as claimed in claim 1, wherein said nonionic surfactant (B) is selected from the group consisting of nonionic surfactants having 1 to 50 moles, on average, of a polyoxyalkylene group per mole of hydrophobic group, a sugar-series nonionic surfactant and a mixture thereof.

6. A skin cleanser as claimed in claim 1, wherein the viscosity of said detergent composition ranges from 1 to 100 cps (at 25° C.).

7. A skin cleanser as claimed in claim 1, wherein the foam density of said detergent composition ranges from 0.03 to 0.25 g/ml.

8. A skin cleanser as claimed in claim 1, wherein said foamer container is provided with two or more porous membranes which are nets of 50 to 500 mesh.

9. The skin cleanser of claim 1, wherein said anionic surfactants having a branched hydrocarbon group are phosphate surfactants represented by the formula (1).

10. A skin cleanser as claimed in claim 5, wherein said nonionic surfactants having 1 to 50 moles, on average, of a polyoxyalkylene group are selected from the group consisting of polyoxyalkylene alkyl ethers, polyoxyalkylene fatty acid esters, polyoxyalkylene sorbitan fatty acid esters, polyoxyalkylene sorbitol fatty acid esters, polyoxyalkylene glycerol fatty acid esters, polyoxyalkylene alkylamines, polyoxyalkylene alkyl fatty acid amides, and polyoxyalkylene alkylphenyl formaldehyde condensates.

11. A skin cleanser as claimed in claim 5, wherein said sugar-series nonionic surfactant is selected from the group consisting of alkylsaccharide-series surfactants, sugar amide-series surfactants and sucrose fatty acid ester-series surfactants.

12. A skin cleanser as claimed in claim 11, wherein said alkylsaccharide-series surfactant is a compound represented by the following formula:

$R^6$—O—$(R^7O)_aG_b$ wherein $R^6$ represents a linear or branched alkyl, alkenyl or alkylphenyl group having 6 to 18 carbon atoms, $R^7$ represents an alkylene group having 2 to 4 carbon atoms, G represents a reducing sugar having 5 to 6 carbon atoms, a is a number from 0 to 10 and b is a number from 1 to 10.

13. A skin cleanser as claimed in claim 11, wherein said sugar amide-series surfactant is a compound represented by the following formula:

$R^8$—CO—$NR^9X^3$ wherein $R^8$ represents a linear or branched alkyl, alkenyl or alkylphenyl group having 5 to 18 carbon atoms, $R^9$ represents a hydrogen atom, a linear or branched alkyl or alkenyl group having 1 to 18 carbon atoms, —$CH_2CH_2OH$, —$CH_2CH(OH)CH_3$, —$CH_2CH_2CH_2OH$, or —$(CH_2CH(R^{10})O)_c$—H, wherein $R^{10}$ represents a hydrogen atoms or a methyl group and c is a number from 0 to 10, and $X^3$ represents a polyhydroxyalkyl group representing a sugar residue having 4 to 30 carbon atoms.

14. A skin cleanser as claimed in claim 11, wherein said sucrose fatty acid ester-series surfactant is a compound represented by the following formula:

wherein $R^{11}$, $R^{12}$ and $R^{13}$ independently represent each a hydrogen atom or a linear or branched, saturated or unsaturated acyl group having 8 to 24 carbon atoms, provided that $R^{11}$, $R^{12}$ and $R^{13}$ are not simultaneously hydrogen.

* * * * *